United States Patent [19]

Field

[11] Patent Number: 4,465,232

[45] Date of Patent: Aug. 14, 1984

[54] DEVICE FOR CARRYING A SCENTED ELEMENT FOR AFFIXING TO THE BODY, ARTICLES OF CLOTHING OR PACKAGES

[76] Inventor: Florence F. Field, 180 West End Ave., New York, N.Y. 10023

[21] Appl. No.: 384,865

[22] Filed: Jun. 4, 1982

[51] Int. Cl.³ .............................. A61L 9/04; G09F 3/00
[52] U.S. Cl. ................................................. 239/36; 2/170;
2/DIG. 11; 239/60; 428/52; 428/79; 428/905; 428/906.6
[58] Field of Search ................ 428/905, 7, 52, 79, 428/906.6; 2/59, 60, 170, DIG. 11; 24/255 SL, 375; 239/36–53, 57–60

[56] References Cited

U.S. PATENT DOCUMENTS

| | | | |
|---|---|---|---|
| 1,587,387 | 6/1926 | Lichtman | 428/906.6 X |
| 1,743,827 | 1/1930 | Mercogliano | 239/60 |
| 1,831,677 | 11/1931 | March | 239/57 |
| 2,425,333 | 8/1947 | McCarl | 2/59 |
| 2,574,678 | 11/1951 | Wilbur | 2/60 X |
| 2,626,833 | 1/1953 | Valentine | 428/905 X |
| 2,717,174 | 9/1955 | Casanovas | 428/905 X |
| 3,945,568 | 3/1976 | Bychowski | 428/905 X |
| 3,947,971 | 4/1976 | Bauer et al. | 239/60 X |
| 4,228,954 | 10/1980 | Rosenzweig | 428/71 X |
| 4,254,910 | 3/1981 | Martin | 239/60 |
| 4,277,024 | 7/1981 | Spector | 428/905 X |
| 4,283,011 | 8/1981 | Spector | 428/905 X |

Primary Examiner—Henry F. Epstein
Attorney, Agent, or Firm—Auslander & Thomas

[57] ABSTRACT

An adornment having a front face, preferably decorated, and a rear face. The rear face preferably has an adhesive layer thereon for fixing the adornment to another surface. The front face of the adornment has a pocket formed therein for receiving a scented element, preferably a scent saturated pellet or a scent-filled capsule.

5 Claims, 5 Drawing Figures

FIG.1  FIG.2
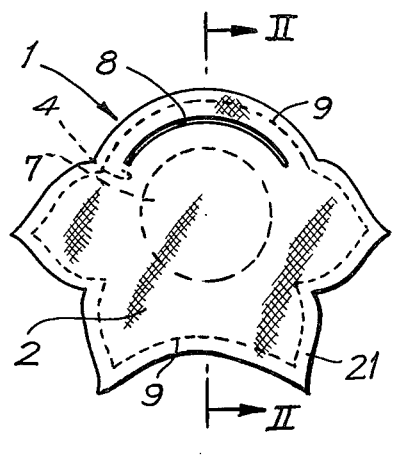 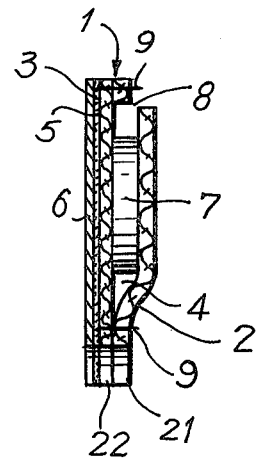
FIG.3  FIG.4
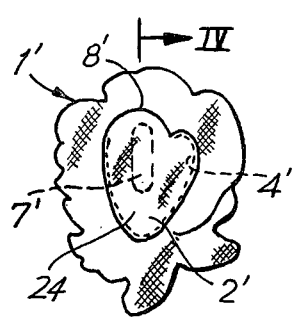 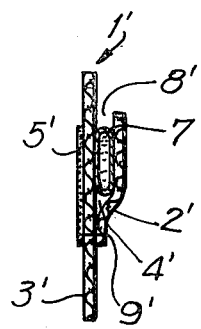
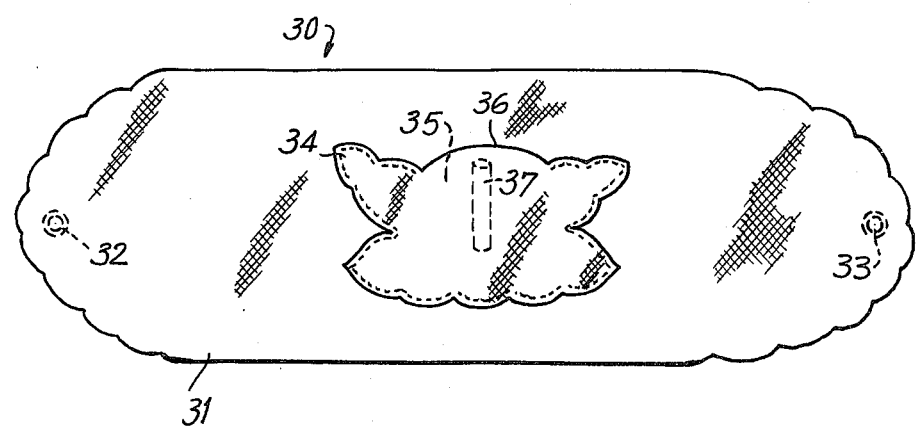
FIG.5

DEVICE FOR CARRYING A SCENTED ELEMENT FOR AFFIXING TO THE BODY, ARTICLES OF CLOTHING OR PACKAGES

BACKGROUND OF THE INVENTION

The present invention relates a device for carrying a scented element for affixing to the body, articles of clothing or packages, either obviously or secretly.

SUMMARY OF THE INVENTION

The main object of the present invention is to provide an adornment which may have a decorative face and means forming a pocket therein for receiving a scented element such as a capsule, a scent saturated pellet or the like.

One face of the adornment has means for fixing same to another surface and preferably comprises an adhesive layer and preferably a removable backing layer thereon.

In a preferred embodiment a decorative applique face is preferably formed for the adornment with at least two fabric layers with the pocket formed therebetween by an opening between the two layers. Alternatively, the decorative face comprises embroidery on a fabric layer with the pocket being formed therebetween.

The scented pellet can be in the shape of a lozenge or disc, a rod, etc., and can be scented with perfume, toilet water or other fragrances.

Another object of the invention is to provide a clothing accessory such as a cuff which can be releasably wrapped around the wrist, neck, head, etc. and means forming a pocket in one face thereof for receiving a scented element of the type mentioned hereinabove.

Although such novel features are believed to be characteristic of the invention and are pointed out in the claims, the invention in the manner in which it may be carried out, may be further understood by reference to the description following and the accompanying drawings wherein:

BRIEF DESCRIPTION OF THE DRAWINGS

FIG. 1 is a top view of an adornment according to the present invention;

FIG. 2 is a sectional view along line II—II in FIG. 1;

FIG. 3 is a top view of another embodiment of an adornment according to the present invention;

FIG. 4 is a sectional view along line IV—IV in FIG. 3; and

FIG. 5 is a top view of a clothing accessory according to the invention.

DETAILED DESCRIPTION OF THE PREFERRED EMBODIMENTS

Referring to FIGS. 1 and 2, one embodiment of the adornment 1 according to the invention is shown having a decorative face 2 and a rear face 3 on which a pressure-sensitive adhesive 5 is applied along with a removable paper backing layer 6. The decorative face 2 is formed by a layer of embroidery 21 on the fabric face 2 which is a fabric layer and which is stitched thereon at the peripheries by stitches 9. In the convenient location shown, an opening 8 is provided which is the inlet to the pocket 4 formed between the two layers 3 and 2. Inserted in the pocket 4 is a scent-soaked pellet 7 which has the form of a disc or lozenge.

In FIGS. 3 and 4, an adornment 1' is shown having a decorative face 2' and a rear face 3' on which a conventional pressure-sensitive adhesive layer 5' is provided. The decorative face 2' is formed by a multi-layered piece of embroidery including the rear face 3' in the form a layer and the front face 2' in the form of a layer which are stitched together at their peripheries by stitching 9', save for an opening 8' which acts as an inlet for a pocket 4' formed between the faces 2' and 3'. Insertable in the pocket 4' is a scent-filled capsule 7' which is received therein and ruptured to release the scented liquid contained therein.

The adornments 1, 1' are composed of fabric and can be made in any of a range of sizes from ½" square to 3" square. While the scent-filled capsule 7' can be used for a delayed scenting, the scent saturated pellet 7, composed of felt or the like, immediately diffuses into the adornment and the surrounding area. The scent may be perfume, toilet water or other conventional fragrances.

To use the adornment 1, one removes the backing layer 6, permitting the tacky adhesive layer 5 to stick onto any available mounting surface, such as fabric, paper or the like. Adornment 1' can be used to effect a more permanent mounting since it will iron-on to another fabric surface, i.e., a garment. The pellet 7 or capsule 7' can then be inserted in the pocket 4, 4' after the adornment is mounted in place.

The use of embroidery is to make the adornment of the present invention attractive for display. The adornment 1 of the present invention is particularly suited for female use. The adornment 1 of the present invention is not limited exclusively to female use. It can be attractively configured for male use in conjunction with masculine cologne fragrances. The configuration of the present invention with its adhesive layer 5 adapts the adornment 1 for optional male use or female use where desired, concealed, in the case of a male, such as behind a lapel or under a collar.

It should be noted that the shape of the element 7 can be configured as desired to be completely enclosed in the pocket 4 or to be partially exposed and form part of the design of the decorative face 2 of the adornment, for example, the stamen or pistil of a flower.

FIG. 5 shows a clothing accessory 30, which, depending upon the shape of elongated fabric member 31, can be a cufflet, a choker, a collar, a headband, etc. Disposed on the opposite ends of the member 31 are means for releasably connecting the ends, which in the embodiment shown, comprises male and female snap connectors 32, 33. The accessory 30 further comprises a decorative fabric member 34, such as a piece of embroidery or an applique which is mounted on one face, save for an opening 36 which serves as an inlet for a pocket 35 formed between members 34 and 31. Received in the pocket 35 is a scented element 37, which is shown in the form of a scent saturated rod, but which may have alternative configurations or may be a scent-filled capsule.

The adornment according to the present invention and shown by way of example in FIGS. 1-4, has many advantageous uses. For example, they can be used for mailings together with monthly statements to introduce new fragrances, for commercial and industrial uses in promoting new fragrances. They can be used for personal enhancement as an addition to one's wardrobe in which the user has an assortment of adornments for different outfits. They can be applied to female underwear in which the wearer might apply one to the top of a brassiere or slip so that the fragrance permeates through outer garments. It is envisioned that airline attendants can wear embroidered appliques which have the airline insignia and which hold a fragrance to mask airplane odors during their work. Similarly, athletic team members can wear adornments configured with their team insignia and scented.

The adornments can be used on stationery where a decorative floral design can be attached to an appropriate fragrance. Men in uniform, such as doormen, can wear the adornments behind their lapels and it can be scented with a cologne. Women can wear the appliques on their outer garments, such as on a cuff or a collar. Little girls can wear them on a party dress or on everyday clothing in order to get them accustomed to wearing perfume.

The adornment can be packaged and displayed on a department store rack or in a supermarket at the cash register. They can be used for sampling perfumes in cosmetics departments in place of flagons and sprays, or as a premium to induce the pur of a larger perfume package.

In packaging, they can be put on tissue paper wrapping or used in a bow or on the outer wrapping paper.

They can also be used as ornaments on shoes, as ornaments on a headband, as ornaments on purses, hats or belts. They can be given to women at restaurants, used as bookmarks or as party favors.

It is also envisioned that the adornments be sold separately, that the pellets be sold separately as a refill and that the adornments and pellets be sold together.

The terms and expressions which are employed herein are used as terms of description only and it is recognized that various modifications are possible with the scope of the invention claimed.

It is also understood the following claims are intended to cover all of the generic and specific features of the invention herein described, and all statements of the scope of the invention which, as a matter of language, might fall therebetween.

What is claimed is:

1. A fabric adornment for the free emission of scent comprising a decorative textured embroidered fabric front face, a fabric rear face, adhesive means disposed on said rear face adapted to fix said adornment to another surface, said front face and rear face forming a pocket having one permanently open side on said front face, and said pocket adapted to slidably receive and remove a scented element in the form of a scent impregnated lozenge, whereby an adornment is adapted to provide scent over a protracted period of time.

2. The fabric adornment of claim 1, further including a removable backing sheet on said adhesive means.

3. In combination: a fabric adornment comprising a decorative textured embroidered fabric front face, a fabric rear face, adhesive means disposed on said rear face adapted to fix said adornment to another surface, said front face and rear face forming a pocket having one permanently open side on said front face, and a scented element in the form of a scent impregnated lozenge adapted to be slidably received and removed therefrom.

4. A clothing accessory comprising: an elongated fabric member, means for releasably connecting the ends of said fabric member, and a smaller decorative textured embroidered fabric front face, said front face and elongated member forming a pocket having one permanently open side on said front face, said pocket adapted to slidably receive and remove a scented element in the form of a scent impregnated lozenge.

5. The accessory according to claim 4, wherein the releasable connecting means comprises snap-fastening elements.

* * * * *